United States Patent [19]

Blackman et al.

[11] Patent Number: 5,013,545

[45] Date of Patent: * May 7, 1991

[54] AQUEOUS GELS CONTAINING TOPICAL MEDICAMENTS

[75] Inventors: Steven Blackman, New York; Irene Ralske, North Bellmore, both of N.Y.

[73] Assignee: Thames Pharmacal Co., Inc., Ronkonkoma, N.Y.

[*] Notice: The portion of the term of this patent subsequent to May 29, 2007 has been disclaimed.

[21] Appl. No.: 130,445

[22] Filed: Dec. 9, 1987

[51] Int. Cl.$^5$ .................. A61K 31/045; A61K 47/12; A61K 47/38; A61K 31/13

[52] U.S. Cl. .................................. 424/81; 424/443; 424/445; 424/447; 424/449; 514/781; 514/785; 514/887

[58] Field of Search .............. 514/171, 179, 212, 242, 514/399, 424, 514, 520, 549, 714, 781, 785, 887; 424/81, 128, 443, 445, 447, 449

[56] References Cited

U.S. PATENT DOCUMENTS

| | | | |
|---|---|---|---|
| 4,166,177 | 8/1979 | Cragoe, Jr. et al. | 424/81 X |
| 4,247,547 | 1/1981 | Marks | 424/81 |
| 4,316,887 | 2/1982 | Kamishita et al. | 424/81 X |
| 4,525,347 | 6/1985 | Inagi et al. | 424/81 X |
| 4,525,348 | 6/1985 | Arizono et al. | 424/81 |
| 4,537,776 | 8/1985 | Cooper | 514/549 |
| 4,540,572 | 9/1985 | Seth | 424/81 X |
| 4,557,934 | 12/1985 | Cooper | 514/399 |
| 4,593,048 | 6/1986 | Sato et al. | 514/778 |
| 4,702,916 | 10/1987 | Geria | 514/514 |

FOREIGN PATENT DOCUMENTS

| | | |
|---|---|---|
| 0068552 | 6/1982 | European Pat. Off. . |
| 0091964 | 9/1982 | European Pat. Off. ............ 514/778 |
| 1465665 | 2/1977 | United Kingdom . |
| 2017491 | 8/1978 | United Kingdom . |

*Primary Examiner*—Merrell C. Cashion, Jr.
*Assistant Examiner*—Carlos Azpuru
*Attorney, Agent, or Firm*—Kirschstein, Ottinger, Israel & Schiffmiller

[57] ABSTRACT

Aqueous gel compositions incorporate topically active pharmaceutical agents in a non-irritating gel comprising from about 60 to about 90% ethyl alcohol and from about 0.5 to about 30% water together with at least one gelling agent. Optional additives include gel enhancers, gel neutralizers, ultraviolet absorbers, gel clarifying agents, anti-irritants and moisturizers. The gel compositions exhibit good bactericidal and bacteriostatic activity in addition to the pharmaceutical activity of the active topical ingredient. Methods of treating skin areas in mammals requiring topical medication comprise the application of the gel, with or without the incorporation of a topically active ingredient, to the affected skin areas 1 to 5 times daily.

28 Claims, No Drawings

AQUEOUS GELS CONTAINING TOPICAL MEDICAMENTS

BACKGROUND OF THE INVENTION

1. Field of the Invention

The present invention relates to aqueous gels having topical pharmaceutical activity, and methods of treating topical conditions by using said gels.

2. Description of the Prior Art

Pharmaceutical agents effective in topical application, e.g., for treating dermatological conditions, generally must be incorporated into a suitable ointment, gel, lotion or cream vehicle to promote uniform application and effective transdermal absorption.

It is often desirable in treating certain topical conditions with agents such as antifungals, antihistamines or anti-inflammatory drugs to concomitantly apply a bactericidal and/or bacteriostatic (antiseptic) agent to the skin to prevent bacterial infection or re-infection of the affected area. Rather than applying the primary topical agent and the bactericidal or antiseptic agent separately, it has been proposed to administer the primary agent (e.g., antifungal or anti-inflammatory) in a vehicle or matrix which itself possesses a high degree of bactericidal or bacteriostatic activity.

Ethyl alcohol, also known as ethanol or more simply "alcohol", is known to be highly bactericidal in high concentration. Topical liquid preparations comprising a dermatologically active agent dissolved or suspended ethyl alcohol, which preparations display both bactericidal activity and the activity of the dissolved or suspended agent, are known in the prior art. Such liquid alcohol-containing preparations suffer from a number of drawbacks, however. While ethyl alcohol is bactericidal in high concentrations, it exhibits poor bacteriostatic or antiseptic activity and infection or re-infection of the treated area not long after application of liquid alcohol-containing preparations is common. Furthermore, while alcohol in liquid form enhances the penetrability of the dissolved pharmaceutical agent for a brief period of time, the alcohol applied to exposed areas quickly evaporates and does not exhibit a long-term absorption-enhancing effect. Liquid alcohol-containing preparations are also inconvenient to store, carry and apply, and much spillage and waste is entailed in the application of such preparations.

Alcohol-containing gels and gel-like vehicles for pharmaceutical agents are known in the prior art. By way of example, U.S. Pat. No. 4,540,572 discloses a gel-like ointment containing indomethacin as well as alcohol to be applied topically, but intended to achieve systemically significant blood levels of the indomethacin for treatment of inflammatory and degenerative rheumatic diseases, not for topical therapy. There is no disclosure in that patent, however, of any bactericidal or antiseptic activity for the vehicles taught, and indeed, the concentration of alcohol in the vehicles (30–50%) is insufficient to exhibit significant antimicrobial activity.

U.S. Pat. No. 4,593,048 teaches compositions including high concentration of lower alcohols and systemically active pharmaceutical agents, whereby the compositions are applied topically (including in gel form) but the active ingredient is intended to be absorbed percutaneously into the bloodstream. No disclosure of the use of such composition for treatment of topical inflammations, dermatoses, etc. is included in that patent; nor is there any teaching of gels containing high alcohol concentrations with topically active ingredients as well as significant concentrations of water. The lack of water in the gel compositions containing substantial alcohol concentrations significantly decreases their antiseptic potency. Addition of water to the gels disclosed in U.S. Pat. No. 4,593,048 which already contain high alcohol concentration would destroy their gel-like consistency.

Hence, the prior art does not teach topical compositions containing high concentrations of alcohol in a form which maximizes its bactericidal and antiseptic properties and enables it to act as a long term penetration enhancer for a topically active pharmaceutical agent.

SUMMARY OF THE INVENTION

It is an object of the present invention to provide gel compositions for use in treating conditions requiring topical medication, such as dermatological diseases, which comprise high concentrations of alcohol, water and topically effective pharmaceutical agents in a gel matrix.

A further object of the present invention is to provide compositions as aforesaid which promote and enhance the penetration and, accordingly, the topical activity of any suspended or dissolved pharmaceutical agent.

Yet another object of the present invention is to provide compositions as aforesaid which are stable, easy to store and to apply, and which may be utilized with a minimum of wasteful spillage.

Still a further object of the present invention is to provide methods of treating topical conditions utilizing the novel gel compositions.

In keeping with these objects and others that will become apparent hereinafter, the present invention resides, briefly stated, in gels for topical use containing from about 60 to about 90% by weight ethyl alcohol, from about 0.5 to about 30% by weight water, and from about 0.5 to about 5% of at least one gelling agent capable of gelling the alcohol-water system, together with a pharmaceutically effective amount of a topical pharmaceutical agent. The topical pharmaceutical agent may be selected from any of the known antihistaminic agents, anti-inflamatory agents, antimicrobials, antifungals and anesthetics.

The subject gel compositions may optionally include gelling enhancers, gel neutralizing agents, counter-irritants, ultraviolet absorbing agents, emollients, humectants, clarifiers and coloring and fragrance additives.

The compositions of the present invention can be packaged in any standard containers known in the pharmaceutical and cosmetic arts to be suitable for storage and dispensing of gels for topical use, including any of a variety of tubes, bottles, pouches, and the like. The compositions are useful for the treatment of any topical condition where the use of the active pharmaceutical ingredient contained in the gel is indicated, and particularly where it is also desirable to apply an antiseptic agent to the affected area.

DETAILED DESCRIPTION OF THE INVENTION

The aqueous topical gel compositions of the present invention comprise from about 60% to about 90% by weight ethyl alcohol; from about 0.5% to about 30% by weight water, preferably purified or distilled; from about 0.5% to about 5% by weight of at least one gelling agent; and a pharmaceutically effective amount of a topically active pharmaceutical agent selected from the group of antihistaminic agents, anti-inflammatory agents, antimicrobials, antifungals and anesthetics.

As used herein, a "pharmaceutically effective amount" of a topically active agent means a percentage concentration of that agent known in the medical and pharmaceutical arts to be safe and effective in treating dermatological conditions—e.g., 0.5-2.5% hydrocortisone, 1-3% diphenhydramine HCl, 1-3% miconazole nitrate, 1-7.5% lidocaine and so forth. Various concentrations may be used in preparing gels incorporating the same active ingredient to provide for variations in the age of the patient to be treated, the severity of the condition and the duration of the treatment.

The gelling agents utilized in the subject compositions can be any agents which create a stable gel matrix in the presence of substantial quantities of alcohol and water. Preferred gelling agents for use in the present invention include the water-soluble, carboxyvinyl polymers known as carbomers or, by their commercial name, "CARBOPOLS" (B. F. Goodrich Chemical Co., Cleveland, Ohio). Carbomers are also alcohol-soluble but require neutralization for use in non-polar systems. A variety of effective neutralizing agents are known, including sodium hydroxide, potassium hydroxide and sodium bicarbonate, but preferred for the purposes of the present invention are polar organic amines such as triethanolamine and tetrahydroxypropyl ethylenediamine. Generally from about 0.2% to about 5% by weight of such neutralizing agents are sufficient to render the carbomer-created gels non-polar.

Optional ingredients in the gel compositions of the present invention include gelling enhancers, counter-irritants, ultraviolet absorbers (to prevent degradation and discoloration of the gels), emollients and humectants. Suitable gelling enhancers include, by way of example, from about 0.1 to about 3% hydroxymethyl- and hydroxyethylcellulose. Suitable counter-irritants for use in the present invention include any additives known in the pharmacuetical and cosmetic arts which decrease pain and itching upon topical application, such as menthol, camphor, methyl salicylate and triethanolamine salicylate.

Any of a variety of ultraviolet absorbers, emollients and humectants may be incorporated into the gels of the present invention to improve their stability, feel, and anti-drying properties when applied to the skin. Benzophenones are known ultraviolet absorbers which are effective in preventing gel degradation, particularly when a transparent or semi-transparent container is used. Effective emollients and humectants include, for example, lactate esters of fatty alcohols and glycerin.

In order to create a transparent gel, which may be preferable for esthetic reasons and for consumer acceptance, a gel clarifying agent may be added to the subject composition. An example of such agents which is highly effective in creating a transparent gel is "COSMEDIA" (Henkel, Ambler, Penna.), which is a polyacrylamidomethylpropane sulfonic acid.

It has been found that the preferred range of alcohol concentration for use in the present invention is from about 60 to about 80%, because compositions containing in excess of 80% alcohol, while suitable for the purposes of the invention, form less stable gels and do not contain sufficient water to maximize the bactericidal and antiseptic potency of the composition. Similarly, the preferred range of water concentrations is from about 8 to about 30% of the total composition.

Due to their high alcohol concentrations, the novel gels do not require any added preservatives.

The gels of the present invention may be prepared by any conventional process known in the pharmaceutical and cosmetic arts. By one preferred procedure, the water (preferably in distilled or purified form) and all but 5-10% of the alcohol are combined with the primary gelling agent and agitated. Any gelling enhancers utilized are added to this phase.

A second phase is prepared by mixing the pharmaceutically effective amount of the active ingredient, generally from about 0.5% to about 5% of the total composition by weight, with the remaining alcohol. If necessary, the mixture may be carefully heated to 60° C. to assist in solubilizing the active ingredient. A small amount (0.05-1% by weight) of an ultraviolet absorber may optionally be added to this phase as may an effective amount of a counterirritant such as menthol. The first and second phases are then rapidly mixed together until a homogeneous gel is obtained.

Humectants and emollients, comprising in total from about 1% to about 10% of the total weight of the composition, and a gelling agent neutralizer, comprising from about 1% to about 5% of the weight of the composition may also be mixed together to form another optional phase, which is preferably mixed into the first phase before addition of the phase containing the active ingredient. Coloring or fragrance additives may be mixed into the final gel product until suitable appearance and odor is obtained.

Any antihistaminic, anti-inflammatory, antimicrobial, antifungal or anesthetic agent which possesses significant topical activity and is soluble or suspendable in an alcohol/water vehicle without suffering significant loss of potency (i.e., a decrease of 10% or more in pharmaceutical activity over a period of one year as a result of degradation or decomposition) may be utilized as the active ingredient of the gel compositions in the present invention. These include, for example, antihistamines such as diphenhydramine HCl, tripelennamine and pyrilamine maleate; anti-inflammatories such as hydrocortisone, triamcinolone acetonide, fluocinonide, fluocinolone acetonide and betamethasone valerate; antimicrobials such as neomycin, gentamycin, polymyxin and clindamycin; antifungals such as miconazole nitrate, clotrimazole, nystatin and haloprogin; and anesthetics such as lidocaine, dibucaine, benzocaine and pramoxine HCl. The subject gels, containing these active ingredients, are of highly beneficial effect in treating a wide variety of dermatological conditions and trauma in humans and other mammals, including, merely by way of illustration, sunburn, insect bites, pruritic dermatoses, eczemas, psoriasis, hives, abrasions, ringworm, and the like.

Among the many advantages of the compositions of the present invention in comparison with prior art topical gels is the fact that the present compositions contain sufficiently high concentrations of alcohol in a novel gel matrix to be bactericidal and bacteriostatic, both of which activities are enhanced by the presence of a significant amount of water. It is believed that the antibacterial effectiveness of ethyl alcohol results from its denaturing of proteins, which occurs much more readily in the presence of water (see, e.g., Morton, H. E., "Alcohols", in *Disinfection, Sterilization and Preservation*, 2nd ed., pp. 301-31, 1976). Moreover, unlike prior art liquid compositions containing high concentrations of alcohol which display only a transient antibacterial effect, the water-containing gel compositions of the present invention have excellent bioadhesion and remain attached to the site of action for a substantial period of time, which, together with their unique gel matrix, enables the full bactericidal and bacteriostatic activity of the alcohol-water mixture to be effectively utilized. Keeping an affected area germ-free for a substantial period of time after treatment with an active pharmaceutical agent is highly important in the treatment of many skin conditions.

The alcohol-containing gels of U.S. Pat. No. 4,593,048, which do not combine high alcohol concentrations with significant amounts of water, do not exhibit good bioadhesion and are not able to maintain bacteriostatic activity at the site of action for substantial periods of time.

The gels of the present invention, due to their high alcohol concentration and the presence of water, also act as good penetration enhancers for the incorporated active pharmaceutical ingredients by altering the stratum corneum and enhancing its permeability. This effect increases the potency of topical agents which must penetrate below the outer skin surface in order to achieve good anti-inflammatory, antifungal, and similar activity.

The composition of the present invention are easy to package in conventional containers, tubes and pouches and have good stability upon long term storage at ambient termperatures. In such tubes, containers and pouches, the gel compositions may be easily transported in an individual's pocket, purse or carrying bag and small quantities may be effectively dispensed for use with little waste and discomfort due to spillage. The compositions are also of pleasant appearance, odor and consistency, and are water washable and non-irritating, all of which promotes and enhances the patient's desire to use the compositions as needed and/or as prescribed by a physician. This is not the case with many prior art topical compositions which, because of their irritating or messy nature, discourage patient use.

Novel methods are also provided by the present invention for the treatment of affected skin areas in mammals requiring topical medication. By these methods, it is possible to provide a sustained bactericidal and bacteriostatic effect to the affected area, either alone or concomitantly with the activity of an added topically active pharmaceutical agent required to treat the underlying condition, e.g., an antihistaminic agent, anti-inflammatory agent, antimicrobial agent, antifungal agent or anesthetic. Said methods comprise the application to affected skin areas of an aqueous, non-irritating gel containing from about 60 to about 90% by weight ethyl alcohol, from about 0.5 to about 30% by weight water, and from about 0.5 to about 5% by weight of at least one gelling agent.

The application of such gels containing high alcohol concentration from 1 to 5 times daily in sufficient quantities to cover the affected area, even without the incorporation in the gel of any separate topically active pharmaceutical agent, will provide a satisfactory antiseptic and bactericidal effect for treatment of, for example, minor abrasions, lacerations, burns, and other skin conditions requiring a topical germicide. Application of the novel gels including an incorporated topically active agent, such as an antihistamine, anti-inflammatory, antifungal, antimicrobial or anesthetic from 1 to 5 times daily in sufficient quantities to cover the affected area will provide a bactericidal and bacteriostatic effect to the treated skin area in addition to the activity of the topically active agent.

The following examples provide detailed illustrations of gel compositions according to the present invention as well as methods of producing the same. These examples are not intended, however, to limit or restrict the scope of the invention in any way, and should not be construed as providing methods, conditions, ingredients or starting materials which must be utilized exclusively to practice the present invention.

EXAMPLE 1

Antihistaminic Gel

Five kilograms of an antihistaminic gel were prepared utilizing the following ingredients:

| Ingredient | Quantity | Percentage of Total (w/w) |
|---|---|---|
| Phase A | | |
| CARBOPOL 940 (carboxyvinyl polymer, B.F. Goodrich Chemical Co., Cleveland, Ohio) | 50.0 g | 1.0% |
| NATROSAL 250 HHF (hydroxyethyl cellulose, Hercules, Inc., Wilmington, Delaware) | 10.0 g | 0.2% |
| Alcohol USP | 2.75 kg | 55.0% |
| Purified Water | 1.44 kg | 28.7% |
| Phase B | | |
| CERAPHYL ($C_{12-15}$ alcohols lactate, Van Dyk & Co., Belleville, New Jersey) | 125.0 g | 2.5% |
| Glycerin | 125.0 g | 2.5% |
| QUADROL POLYOL (tetrahydroxy-propyl ethylenediamine, BASF Wyandotte Corp.) | 135.0 g | 2.7% |
| PHASE C | | |
| Menthol | 15.0 g | 0.3% |
| UVINUL MS-40 (benzophenone, BASF Wyandotte Corp., Parsippany, New Jersey) | 5.0 g | 0.1% |
| Diphenhydramine HCl | 100.0 g | 2.0% |
| Alcohol USP | 250.0 g | 5.0% |
| Phase D | | |
| FDC Blue #1 | 0.0125 g | .00025% |

The alcohol and purified water of Phase A were mixed in a steam-jacketed stainless steel kettle. The Carbopol 940 gelling agent and Natrosal 250 gelling enhancer were sprinkled into the alcohol/water mixture with rapid mixing.

The ingredients of Phase B were accurately weighed and then charged into a separate steam-jacketed stainless steel kettle where they were thoroughly mixed. Phase B was then added to Phase A with continued mixing to form a gel.

The ingredients of Phase C were subsequently mixed and added to the gel with continued agitation until homogeneous. Phase D was then added to the gel and mixing continued until uniform color and consistency were obtained.

EXAMPLES 2-3

Antihistaminic Gels

The procedure of Example 1 was repeated with the relative proportions of the ingredients changed as follows:

| Ingredients | Weight Percentages | |
|---|---|---|
| | Ex. 2 | Ex. 3 |
| CARBOPOL 940 | 1.25% | 1.5% |
| NATROSAL 250 HHF | 0.25% | 0.3% |
| Alcohol USP (Phase A) | 70.0% | 85.0% |
| Purified Water | 12.1% | 0.55% |
| CERAPHYL | 2.5% | .5% |
| Glycerin | 2.5% | 0.5% |
| QUARDOL POLYOL | 3.8% | 4.05% |
| Menthol | 0.5% | 0.5% |
| UVINUL MS-40 | 0.1% | 0.1% |
| Diphenhydramine HCl | 2.0% | 2.0% |
| Alcohol USP (Phase C) | 5.0% | 5.0% |

EXAMPLE 4

Anti-inflammatory Gel

The procedure of Example 1 was followed utilizing 0.5% hydrocortisone in place of the diphenhydramine. In addition, instead of the coloring agent utilized in Example 1, "COSMEDIA" (polyacrylamidomethylpropane sulfonic acid, Henkel, Ambler, Penna.) was used as a clarifying agent. The relative weight percentages of the ingredients were as follows:

| Ingredients | Weight Percentages |
|---|---|
| CARBOPOL 940 | 1.0 |
| NATROSAL 250 HHF | 0.3 |
| Alcohol USP (Phase A) | 55.0 |
| Purified Water | 28.1 |
| CERAPHYL | 2.5 |
| Glycerin | 2.5 |
| QUADROL POLYOL | 2.7 |
| Menthol | 0.3 |
| UVINUL MS-40 | 0.1 |
| Hydrocortisone | 0.5 |
| Alcohol USP (Phase C) | 5.0 |
| COSMEDIA | 2.0 |

A clear, homogeneous gel was obtained.

EXAMPLE 5

Antifungal Gel

The procedure of Example 4 was repeated with 2% miconazole nitrate used in place of the hydrocortisone. A clear gel was obtained utilizing the following weight percentages of the ingredients:

| Ingredient | Weight Percentages |
|---|---|
| CARBOPOL 940 | 1.0 |
| NATROSAL 250 HHF | 0.3 |
| Alcohol USP (Phase A) | 55.0 |
| Purified Water | 26.6 |
| CERAPHYL | 2.5 |
| Glycerin | 2.5 |
| QUADROL POLYOL | 2.7 |
| Menthol | 0.3 |
| UVINUL MS-40 | 0.1 |
| Miconazole nitrate | 2.0 |
| Alcohol USP (Phase C) | 5.0 |
| COSMEDIA | 2.0 |

EXAMPLE 6

Anesthetic Gel

The procedure of Example 4 was repeated with 5% lidocaine used in place of the hydrocortosine. A clear gel was obtained utilizing the following relative weight percentages of the ingredients:

| Ingredient | Weight Percentage |
|---|---|
| CARBOPOL 940 | 1.0 |
| NATROSAL 250 HHF | 0.3 |
| Alcohol USP (Phase A) | 55.0 |
| Purified Water | 23.6 |
| CERAPHYL | 2.5 |
| Glycerin | 2.5 |
| QUADROL POLYOL | 2.7 |
| Menthol | 0.3 |
| UVINUL MS-40 | 0.1 |
| Lidocaine | 5.0 |
| Alcohol USP (Phase C) | 5.0 |
| COSMEDIA | 2.0 |

EXAMPLE 7

Expanded Flora Tests (cidal) vs. 60% ETOH Occluded Under Plastic Chambers

Approximately $10^5$ resident normal perineal microflora (in 50 λ of Triton X-100) were translocated and inoculated onto designated test sites on the forearms of six human subjects (four sites on each forearm). The sites were left to dry for about 10 minutes. 20 λ each 60% ethanol and the composition of Example 1 were then applied to 3 of the inoculated sites (60% ETOH to sites on one arm and the composition of Example 1 to sites on the opposite arm). One site on each forearm was left untreated and served as a control. After allowing the medications to air-dry for approximately 5.0 minutes, the sites were all covered with plastic occlusive chambers and left in place until the time of culture.

In three subjects, cultures were obtained from both forearms at 15.0 minutes, 1 hour, 2 hours, 3 hours and 5 hours. In these samples, no differences were apparent between sites treated with the composition of Example 1 and ethanol in water. Both treatments produced a total "kill" at all the above mentioned time points and no bacteria could be recovered.

The experiment was then repeated in another three subjects as outlined earlier. In this case, the cultures were obtained at 15 minutes, 6 hours and at 24 hours. Two control sites (untreated), one on each forearm, were also sampled at 24 hours. The control sites served as reference points as to the number of microflora following occlusion of inoculated test sites for 24 hours.

The results in subjects 4, 5 and 6 are shown in the following table. The numbers are expressed as $log_{10}$ per 3.2 cm$^2$, which is the size of the skin area that was sampled (cultured):

| | | Total Aerobes log/3.2 cm$^2$ (chamber) | | | |
|---|---|---|---|---|---|
| Subject Number | | Initial Inoculum per 50 ul | (Sampling Time) | | |
| | | | 15 min. | 6 hrs. | 24 hrs. |
| 4 | Composition of Example 1 | 4.98 | 0 | 2.39 | 2.17 |
| | ETOH | 4.98 | 4.20 | 4.32 | 7.20 |
| 5 | Composition of Example 1 | 5.38 | 0 | 0 | 1.69 |
| | ETOH | 5.38 | 2.95 | 4.16 | 6.23 |
| 6 | Composition of Example 1 | 5.69 | 0 | 1.69 | 0 |
| | ETOH | 5.69 | 2.74 | 4.25 | 6.31 |

A significantly higher number of organisms were received from the 60% ethanol treated sites compared to the sites treated with the composition of Example 1 (two to four orders of magnitude differences). By 24 hours, the differences were even more striking. At this point, 60% ethanol treatment was no different from the control untreated sites, whereas significant inhibition was still evident in the sites treated with the composition of Example 1.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims:

1. An aqueous, non-irritating, bactericidal and bacteriostatic gel composition for topical use, comprising:
   (a) from about 60 to about 90% by weight ethyl alcohol;
   (b) from about 0.5 to about 30% by weight water;
   (c) from about 0.5 to about 5% by weight of at least one gelling agent; and
   (d) a pharmaceutically effective amount of a topically active antihistaminic agent selected from the group consisting of diphenhydramine and diphenhydramine hydrochloride, whereby the combination of the above ingredients maintains the treated areas substantially bacteria-free for a prolonged period of time.

2. A composition according to claim 1 which comprises from about 60 to about 80% alcohol by weight.

3. A composition according to claim 1 which comprises from about 8 to about 30% water by weight.

4. A composition according to claim 1 wherein said gelling agent is a carboxyvinyl polymer.

5. A composition according to claim 4 which additionally comprises from about 0.2 to about 5% of a gel neutralizing agent by weight.

6. A composition according to claim 5 wherein said gel neutralizing agent is selected from the group consisting of triethanolamine and tetrahydroxypropyl ethylenediamine.

7. A composition according to claim 1 which additionally comprises from about 0.1 to about 3% gelling enhancer by weight.

8. A composition according to claim 7 wherein said gelling enhancer is selected from the group consisting of hydroxymethyl cellulose and hydroxyethylcellulose.

9. A composition according to claim 1 which additionally comprises a counter-irritant ingredient.

10. A composition according to claim 1 which additionally comprises an ultraviolet absorbing ingredient.

11. A composition according to claim 1 which additionally comprises an emollient or humectant ingredient.

12. A composition according to claim 1 which additionally comprises a gel clarifying ingredient.

13. A composition according to claim 1 wherein said antihistaminic agent is diphenhydramine HCl.

14. A method of treating skin areas in mammals requiring treatment with topical medication having bactericidal and bacteriostatic activity, comprising the application to the skin areas of a gel composition including:
   (a) from about 60 to about 90% by weight ethyl alcohol;
   (b) from about 0.5 to about 30% by weight water;
   (c) from about 0.5% to about 5% by weight of at least one gelling agent; and
   (d) a pharmaceutically effective amount of a topically active antihistaminic agent selected from the group consisting of diphenhydramine and diphenhydramine hydrochloride, whereby the skin areas are kept substantially bacteria-free for a prolonged period of time.

15. A method according to claim 14 wherein said gel composition contains from about 60 to about 80% by weight alcohol.

16. A method according to claim 14 wherein said gel composition contains from about 8 to about 30% by weight water.

17. A method according to claim 14 wherein said antihistaminic agent is diphenhydramine HCl.

18. A method according to claim 14 wherein said gel is applied in sufficient quantities to cover the skin area from 1 to 5 times daily.

19. A composition according to claim 13 which comprises from 1 to 3% diphenhydramine HCl by weight.

20. A composition according to claim 19 which comprises 2% diphenhydramine HCl by weight.

21. A method according to claim 14 wherein the diphenhydramine HCl constitutes from 1 to 3% of the gel composition by weight.

22. A method according to claim 21 wherein the diphenhydramine HCl constitutes 2% of the gel composition by weight.

23. A composition according to claim 20 which additionally comprises about 60% alcohol by weight.

24. A composition according to claim 20 which additionally comprises about 75% alcohol by weight.

25. A composition according to claim 20 which additionally comprises about 90% alcohol by weight.

26. A method according to claim 20 wherein the alcohol constitutes about 60% of the gel composition by weight.

27. A method according to claim 20 wherein the alcohol constitutes about 75% of the gel composition by weight.

28. A method according to claim 20 wherein the alcohol constitutes about 90% of the gel composition by weight.

* * * * *